(12) United States Patent
Reed et al.

(10) Patent No.: US 6,807,860 B1
(45) Date of Patent: Oct. 26, 2004

(54) MULTIPLE ALLOY ROTOR TRANSITION ZONE MEASUREMENT SYSTEM AND METHOD

(75) Inventors: Francis Alexander Reed, Scotia, NY (US); Robert V. Falsetti, Schenectady, NY (US)

(73) Assignee: General Electric Company, Schenectady, NY (US)

(*) Notice: Subject to any disclaimer, the term of this patent is extended or adjusted under 35 U.S.C. 154(b) by 74 days.

(21) Appl. No.: 10/463,441

(22) Filed: Jun. 18, 2003

(51) Int. Cl.[7] ............................................. G01N 9/24
(52) U.S. Cl. .............................. 73/614; 73/599; 73/628
(58) Field of Search ....................... 73/614, 620, 627, 73/579, 588, 597, 599, 616, 584, 628, 622, 625, 641, 586, 629; 148/508, 671, 669

(56) References Cited

U.S. PATENT DOCUMENTS

| | | | | |
|---|---|---|---|---|
| 5,445,029 A | * | 8/1995 | Falsetti et al. ................. | 73/609 |
| 5,469,743 A | * | 11/1995 | Zorn ............................. | 73/627 |
| 5,533,401 A | * | 7/1996 | Gilmore ........................ | 73/622 |
| 5,618,994 A | * | 4/1997 | Falsetti ........................ | 73/602 |
| 5,631,424 A | * | 5/1997 | Nieters et al. ................. | 73/598 |
| 6,065,344 A | * | 5/2000 | Nolan et al. ................... | 73/629 |
| 6,182,494 B1 | | 2/2001 | Reed et al. .................... | 73/1.83 |
| 6,332,935 B1 | * | 12/2001 | Gorman et al. ............... | 148/508 |
| 6,387,197 B1 | * | 5/2002 | Bewlay et al. ............... | 148/669 |
| 6,393,916 B1 | | 5/2002 | Bewlay et al. ................ | 73/606 |
| 6,494,098 B1 | * | 12/2002 | Leybovich ..................... | 73/620 |
| 6,512,982 B2 | | 1/2003 | Yang et al. .................... | 702/34 |

* cited by examiner

*Primary Examiner*—Hezron Williams
*Assistant Examiner*—Jacques M. Saint-Surin
(74) *Attorney, Agent, or Firm*—Nixon & Vanderhye P.C.

(57) ABSTRACT

A method to determine a depth of an internal feature in a forging using an ultrasonic transducer including: collecting data on echoes reflected by the internal feature of ultrasonic signals transmitted into the forging; correcting the collected data to compensate for attenuation of the echoes and signals in the forging, and determining a depth of the internal feature in the forging.

11 Claims, 4 Drawing Sheets

Time (microseconds)
— Ultrasonic Signal Amplitude
✲✲ Corrected Ultrasonic Amplitude for Depth — Raw UT Data
×× Center of Transition Zone
-- Estimated Transition Boundary

MULTIPLE ALLOY ROTOR TRANSITION ZONE MEASUREMENT SYSTEM AND METHOD

BACKGROUND OF THE INVENTION

This invention relates to techniques to locate transition zones in a multi-alloy metal forging. A transition zone is a boundary region in a forging between one metal alloy composition and another met al alloy composition. In particular, the invention relates to measuring the location of a transition zone in a forging using ultrasonic waves.

Using multiple alloys in a forging allows the forged component to have different material properties at different locations of the forging. Forged components are often formed to have material properties, e.g., strength and heat resistance, that vary throughout the component. Incorporating multiple alloys in a forging is one technique to vary the material properties in a forged component.

The use of multiple-alloys raises concerns regarding thermal distortions among the different alloys in a forging. Each of the different alloys in a multiple alloy forging may have different thermal expansion and contraction characteristics. To control the thermal expansion and distortion between zones of different alloys, the transition zone is positioned to avoid undue thermal distortions caused by differences in the coefficients of thermal expansion among the different alloys in the forging.

The location of the transition zone between the alloys in the component is measured as part of a determination to predict the amount of distortion that a forged component will experience at different temperatures. A nondestructive technique is needed to locate transition zones in a forging to, for example, perform a thermal distortion analysis of the forging.

Conventional methods for locating a transition zone include chemical analysis of the surface of the forging. The internal location of the transition zone is estimated based on the surface data obtained from the chemical analysis and prior knowledge of the shape of the transition zone. This chemical method assumes that the transition zone has a constant shape in each forged component. However, the shape of a transition zone tends to vary from component to component. The chemical method can be inaccurate in determining the position of a transition zone because of variances in the shapes of the zone. A more accurate measurement technique is needed to locate a transition zone.

Ultrasonic measurements of forgings have not been used to measure the location of transition zones. Ultrasonic measurements have been used to monitor the quality of bonds in composite structures. The reflection of ultrasonic waves passing through a forged component is monitored to determine the quality of the bond by detecting porosity or delamination-type defects in the component. In ultrasound bond quality applications, the location of the material interface is known and measurements are not made to locate a transition zone.

Further, ultrasonic thickness gauges are available to measure the thickness of materials. These gauges generally require an easily identifiable and strong ultrasound echo signal, e.g., a backwall ultrasound echo signal, to measure the signal travel time through the material. Transition zones do not provide an easily identifiable signal source for existing ultrasound thickness gauges to analyze and measure. Ultrasonic thickness gauges are not applicable to locating a transition zone in a multiple alloy forging because there is no easily identifiable echo from the transition zone region between alloys.

Ultrasonic beam attenuation and scattering techniques have been used to estimate grain size in forged materials. These attenuation and scattering techniques focus an ultrasonic beam to reduce the scattering from grains in materials. Prior ultrasonic techniques associated with grain scattering primarily relate to the elimination of scattering noise to improve inspection sensitivity. These techniques have not been applied to locate transition zones.

There is a long felt need to identify and measure the location of alloy to alloy transition zones in a multiple alloy forging. The method should be non-destructive and should measure transition zones below the surface of a forged component. It would be helpful if the method used readily available equipment so that the method can easily be implemented in the production of forgings.

BRIEF DESCRIPTION OF THE INVENTION

In a first embodiment, the invention is a method to determine a depth of an internal feature in a forging using an ultrasonic transducer comprising: collecting data on echoes reflected by the internal feature of ultrasonic signals transmitted into the forging;

correcting the collected data to compensate for attenuation of the echoes and signals in the forging; and determining the depth of the internal feature.

In a second embodiment, the invention is a method to determine a depth of an internal feature in a forging having a generally circular cross section using an ultrasonic transducer comprising: collecting data on echoes reflected by the internal feature of ultrasonic signals transmitted into the forging, wherein the data is collected at a plurality of angular positions around a perimeter of the forging; correcting the collected data to compensate for attenuation of the echoes and signals in the forging; partitioning the data to eliminate data corresponding to echoes from surfaces of the forging; identifying a maximum amplitude signal from the partitioned data for each of the angular positions; plotting the maximum amplitude signal data on polar chart and identifying a center of the maximum amplitude signal data, and plotting a circular cross-section of a transition zone coaxial with the center and a radius corresponding to an average value of the maximum amplitude signal data.

In a third embodiment, the invention is a system to determine a depth of an internal feature in a forging comprising: an ultrasonic transducer positioned on a surface of the forging, wherein said transducer transmits ultrasound beams into the forging, receives echoes reflected from internal feature in the forging and generates data signals indicative of the echoes, and a computer receiving the data from the transducer, wherein said computer executes a program to process said data by correcting the data to compensate for attenuation of the echoes and signals in the forging and to determine a depth of the internal feature in the forging.

DETAILED DESCRIPTION OF THE INVENTION

A method to measure the depth of a transition zone between different alloys in a multiple alloy rotor forging has been developed. The method uses ultrasonic waves to collect inspection data from the forging to nondestructively measure the depth of the interface, e.g., transition zone, between the alloys in the forging. The method applies ultrasonic waves to the surface of a forged component to interrogate the interior of forging. The ultrasonic waves reflect off of internal structures, e.g., grain boundaries, within the alloys of the forging. These reflected signals are received, corrected and analyzed to determine the location of the transition zone within the forging.

The method detects an alloy transition zone by analyzing the relatively low amplitude ultrasonic signals from the sound energy scattered by grain boundaries in the forging. The character of the grain boundary for each alloy is distinct. Ultrasound echoes from the grain boundaries provide data regarding the changes in the grain at a transition zone. An indication of the location of a transition zone may be obtained from the echo signals from grain boundaries. The number of grain boundaries is substantially greater in a transition zone, than in an internal region of forging formed of one alloy. The echo signal strength should increase at a transition zone because of the increase in grain boundaries to reflect the beams 16.

Figure 1:
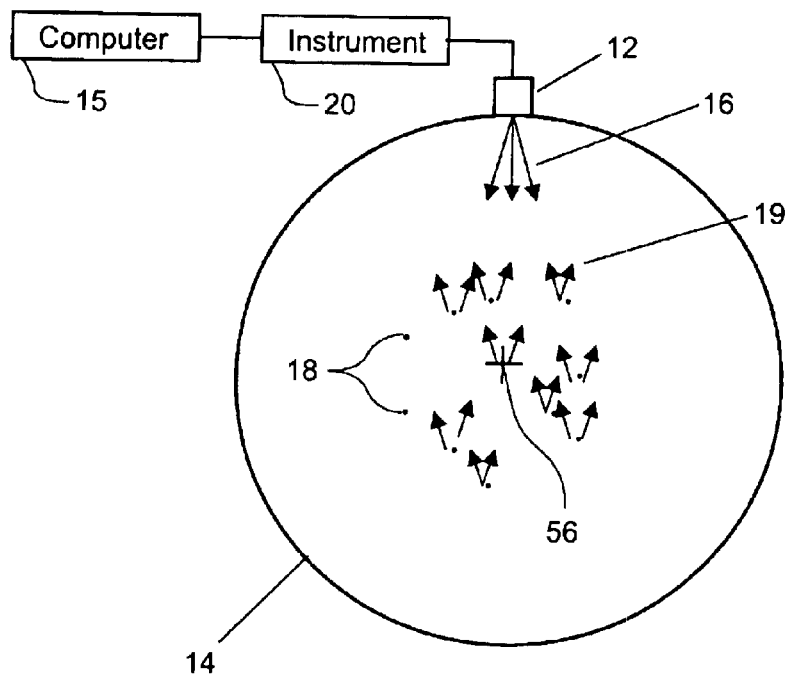
FIG. 1 is a schematic diagram of an ultrasonic measurement system applied to a multi-alloy forging.
Figure 2:
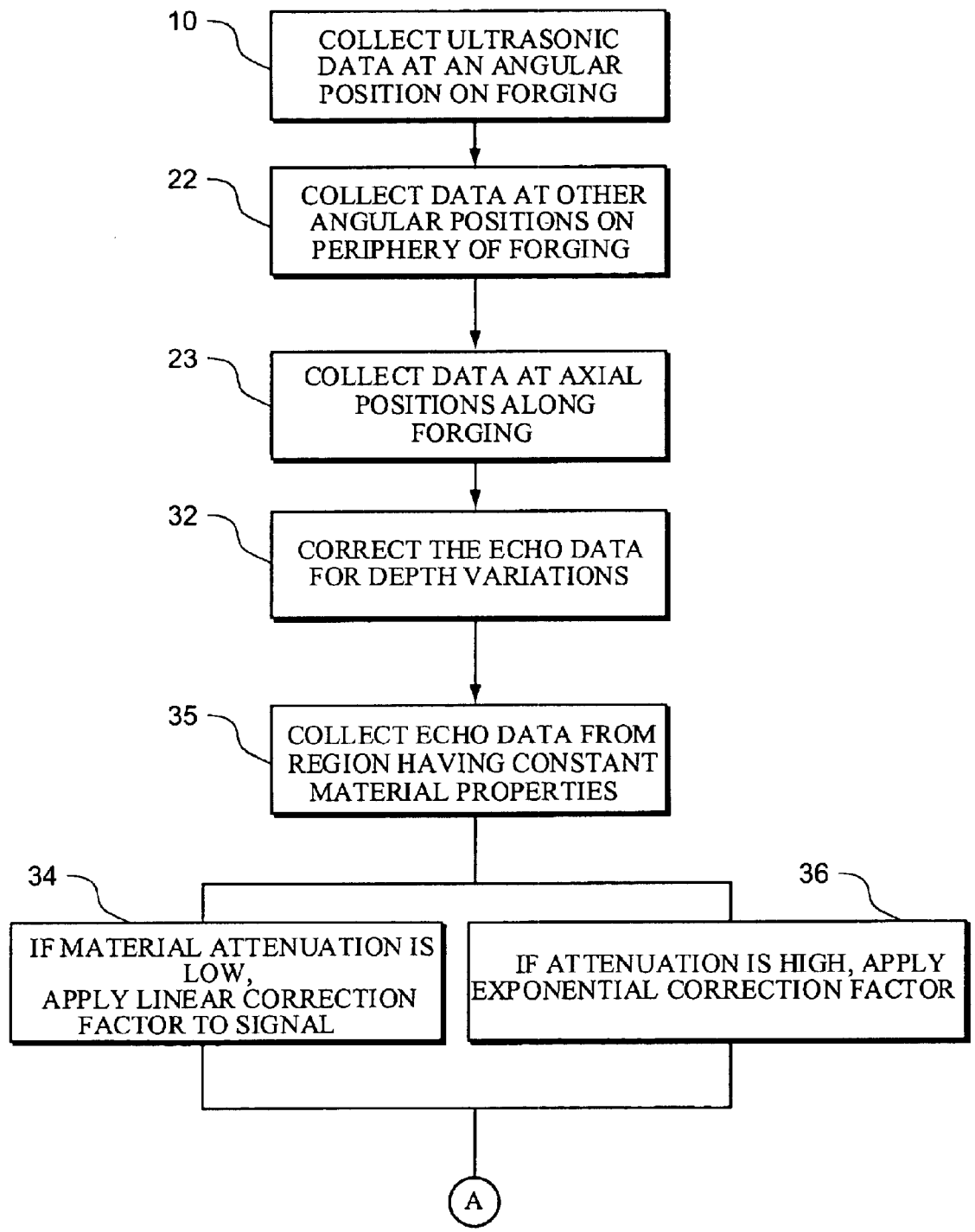
FIGS. 2 and 3 are a flow chart illustrating a method of measuring a transition zone in a multi-alloy forging.
Figure 3:
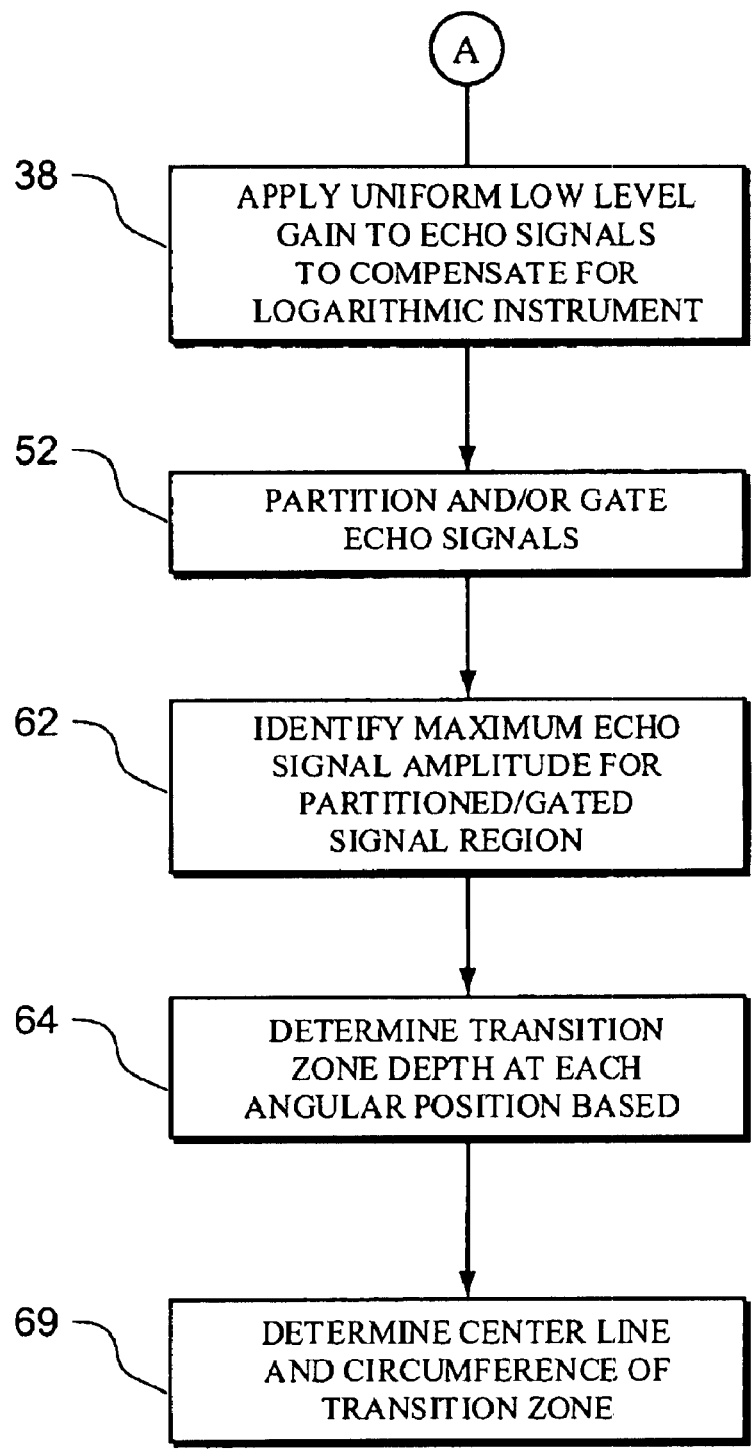

FIG. 1 is a schematic diagram of a multi-alloy forging and an ultrasonic transducer. FIGS. 2 and 3 illustrate an ultrasonic data collection method. In step 10, ultrasonic data is collected from the forging 14. The data is collected using a computer-based automated test system. The data from the ultrasound signals passing through and reflected by the forging is analyzed using a computer 15 after the data collection process.

An ultrasonic transducer 12 is positioned on the periphery of the forging 14. The transducer emits ultrasound beam pulses 16 into the forging at various angular positions of the forging. The ultrasonic waves propagate from the transducer 12 and reflect off of internal structures 18, e.g., grain boundaries and structural features of the forging, e.g. a backwall. The echoes 19 are detected by the transducer 12 which measures the time delays from the emission of the beam 16 and the receipt of each the echoes 19, in step 10. This echo data is collected without damaging the forging. The propagation of ultrasonic waves through the forging does not harm the forging.

After the echo data is collected from a particular angular position around the forging, the transducer 12 is radially indexed to another angular position on the forging, in step 22. Echo data may be collected from each of several selected angular positions around the entire periphery of the forging, only through a selected arc of such angular positions or at other selected positions on the periphery of the forging.

When the ultrasonic data is recorded at each of the selected angular positions around the forging for a given axial position on the forging, the axial position of the transducer is indexed to another axial position on the forging, in step 23. At the new axial position, ultrasonic data are again collected at selected angular positions around the circumference of the forging. This process of collecting ultrasound echoes at various angular positions around a circumference of a forging and axially shifting the transducer to another axial position is repeated until the entire region containing the transition zone in the forging is interrogated with ultrasonic beams.

Figure 4:
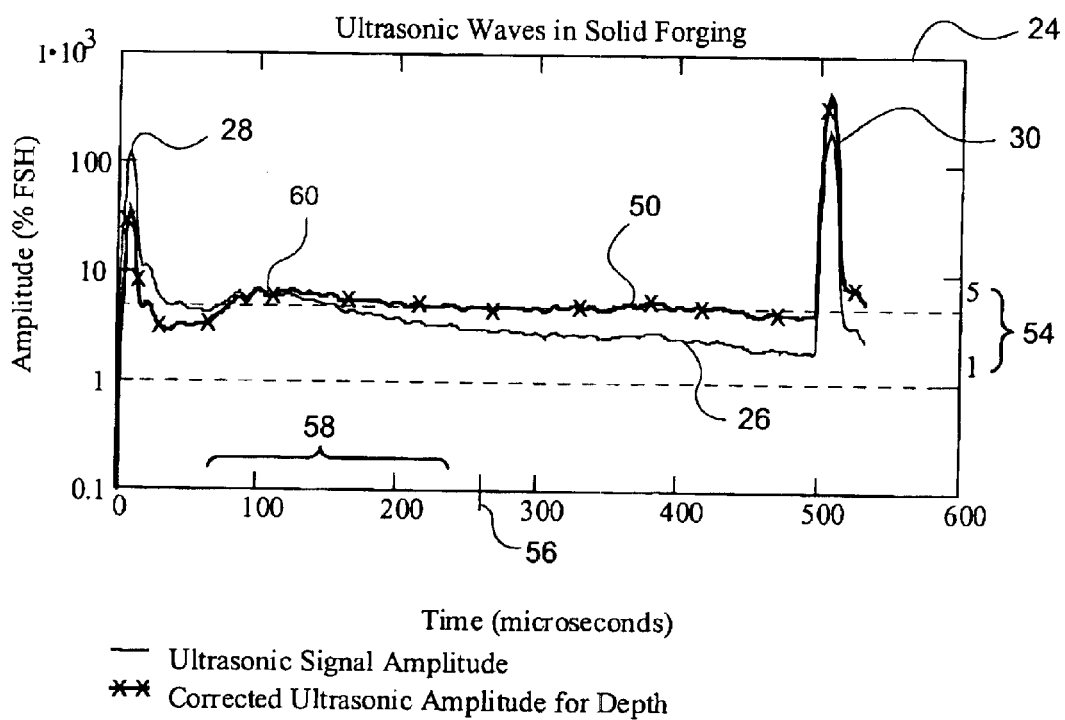
FIG. 4 is a chart of echo signals received by an ultrasound transducer.

FIG. 4 is a chart 24 illustrating an example of the ultrasonic wave data collected at one angular position on the periphery of the forging at one axial position. The chart 24 shows the amplitude and delay time for ultrasound echo signals received from a solid forging. The chart includes a trace 26 (uncorrected) of the received ultrasonic echo signal amplitudes for a period of about 500 microsecond.

The trace 26 shows a first large amplitude echo signal 28 at approximately 0 microseconds and a second large amplitude signal 30 at the end of the data around 500 microseconds. The first echo signal 28 represents the reflection of the transducer pulse off 16 the front surface of the forging. The second echo signal 30 represents a reflection off the back surface of the forging. Theses first and second signals 28, 30 have much higher amplitudes than do echo signals 19 that result from reflections from internal microscopic grain structures 18 in the forging 14. Between the two high amplitude echoes (representing opposite sides of the forging), there are echo signals 19 ranging from two to five percent of the full screen height (FSH) of the chart. These smaller amplitude signals 19 represent echoes from the internal structures within the forging.

Figure 5:
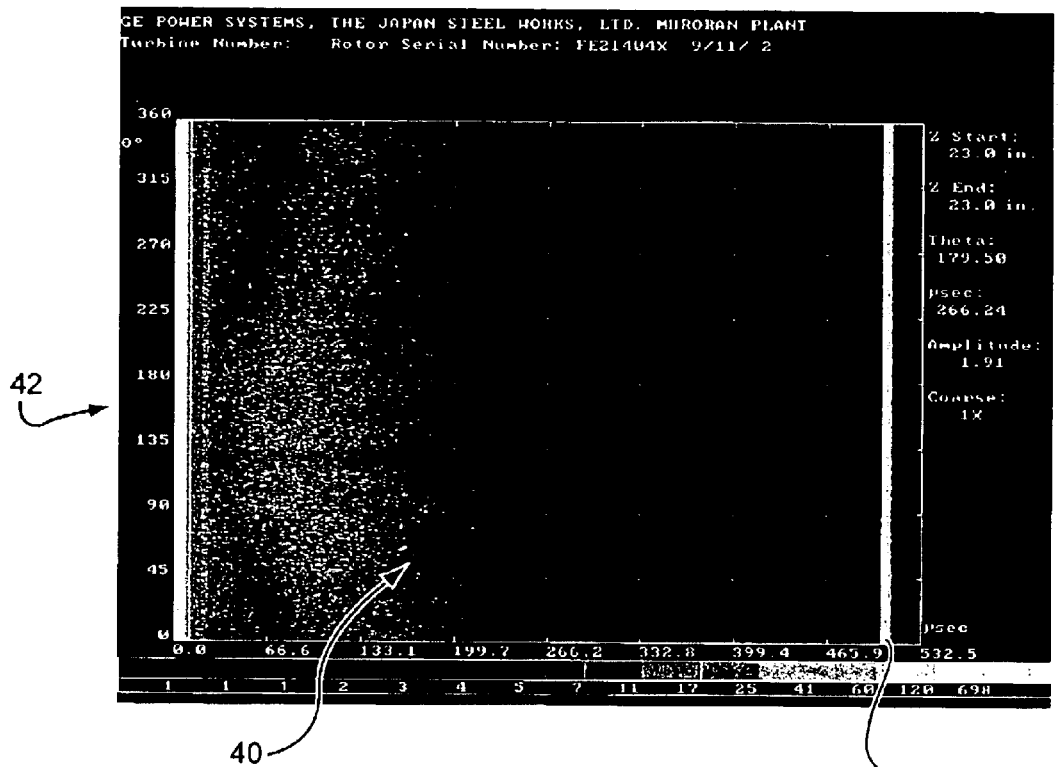
FIG. 5 is an image of ultrasonic data.

FIG. 5 is a chart showing an image 40 of ultrasonic echo data collected by a transducer 12 around the periphery of a forging 14 at one axial position. The rows 42 of the image correspond to the ultrasonic echo signals collected at a particular angular position around the circumference of the forging. Each row represents a particular angular position, such as 180 degrees, on the forging. The horizontal position 44 of the image indicates the time between the transmission of a beam 16 and the reception of an echo signal by the transducer. The time periods 44 are representative of the depth in the forging at which the beam was reflected. In particular, the longer time periods, e.g., above 400 microseconds, indicate that the beam was reflected deep in the forging. The gray scale value or intensity (brightness) of a given picture element in the image 40 corresponds to the ultrasonic amplitude at that location in the forging.

The ultrasonic echo signals are processed to correct the echo data for depth variations, in step 32. Variations occur in the echo signals due to diffraction and attenuation of the beam and reflected echoes pass through the forging. As is evident by the uncorrected signal data trace 26 in FIG. 4, the amplitudes of the data becomes increasingly attenuated as the depth increases at which the echo is reflected. This attenuation can also be seen in FIG. 5 where the intensity of the signals is strongest close to the forging surface, e.g., 0 to 100 microseconds, and becomes increasingly attenuated at longer echo times. To determine the actual depth at which the echo signals are reflected, the returned echo signals should be correction for diffraction and material attenuation.

For alloy materials that have low acoustic attenuation due to distance traveled, the amplitude from internal structures 18, such as grain boundaries, varies inversely and linearly with respect to the depth of the forging. For forging materials that have low acoustic attenuation, the signal attenuation can be compensated for by a linear correction factor that is proportional to the depth from the transducer to the structure in the forging that reflected the beam, in step 34. The value for the linear correction may be determined by analyzing echo data for regions of a forging having constant material properties, e.g., no alloy transitions, in step 35. The constant regions should have a relatively constant echo amplitude throughout the depth of the region. The linear correction is a constant coefficient that, when multiplied, by the depth (time) of an echo signal, renders the amplitude of the echoes to be uniform.

A linear correction factor may not be suitable for forging materials that attenuate ultrasonic beams to a high degree. Where attenuation is high, the amplitudes of the collected echo signals are multiplied by a constant factor that is proportional to the depth of the reflected beam raised to a power other than one. A constant corrector factor raised to the power of one corresponds to the linear correction factor discussed above.

The exponential power value needed to correct the echo data may be determined based on data of ultrasonic signals collected from a region of uniform material properties in a forging, in step 36. The signal amplitude corresponding to an area of uniform material should be constant throughout the depth of the region. A trend of reduced echo amplitude as the echo depth increases in a region of uniform material is indicative of echo attenuation and scattering. In step 35, echo data of a region of constant material property is used to derive an exponential correction factor that converts the amplitudes of the actual data to a constant amplitude value through the depth of the constant region. The exponential power value may be derived using conventional mathematical curve fitting techniques.

The exponential correction factor is applied when processing echo data taken from other forgings formed of similar materials. These other forgings may have multiple alloys and transition zones to be measured. By correcting the echo data for attenuation and scattering affects, the echo data may be more easily analyzed to locate a transition zone.

A linear inverse relationship may not exist between the amplitude of echo data and the depth of the structure that reflected the echo when a logarithmic receiver instrument 20 is used in the transducer 12.

Logarithmic ultrasonic instruments 20 often have a minimum detectable signal level feature that is set to a nominal signal value, such as one percent of the full screen height (FSH). This nominal signal value may automatically applied when the amplitude of the actual data is below the nominal value. For example, if the signal amplitude is below one percent of FSH, then the logarithmic instrument may display a signal amplitude of one percent FSH. This low level nominal adjustment by the instrumentation can introduce an error into the low amplitude signals that are reflected from grain boundaries and other internal sources of echo reflections. Additionally, logarithmic instruments tend to behave nonlinearly close to their saturation point, e.g., at one percent of FSH. In step 40, a uniform gain 54 is applied to the echo signals generated by a logarithmic transducer to raise the amplitude of all of the signals. By raising the amplitude of all echo signals, the effects of the low level adjustment feature in logarithmic instruments can be avoided.

If the ultrasonic signal amplitude values cannot be raised to avoid an instrument nonlinearity, a correction factor may be applied to the echo signals that is proportional to the depth raised to a power less than one, in step 38. A less than one power correction factor may reduce the errors caused by the instrument when analyzing low level echo signals to measure the depth of grain boundaries. This depth exponent can be determined by collecting the amplitude of the ultrasonic signals from within the forging in a region of uniform material properties. A value of the exponent is determined that will provide a constant amplitude value for the ultrasonic signals throughout the depth of the uniform region. A depth exponent values in the range of 0.5 to 0.75 generally provides an acceptable correction power factor for cases where a less than one power correction factor is needed.

FIG. 4 illustrates an example of correcting the ultrasonic signals for depth using a correction power factor of less than one. The corrected ultrasonic signal amplitude values 50 were obtained by multiplying the uncorrected signal trace 26 by a factor proportional to the depth raised to the power of 0.5. The corrected values 50 for the ultrasonic signals are uniform for echo signal travel times of 200 microseconds to 450 microseconds. The amplitudes of the corrected echo signals are uniform through the depth of the forging.

Another step (52) is to partition or gate the ultrasonic data. Partitioning and gating the corrected ultrasonic data removes regions of the echo data that contain ultrasonic signals not related to the internal structure in the forging. The first data region that is removed is the beginning of the ultrasonic data that contains the initial pulse signal 28 corresponding to the surface of the forging. This region 28 can be seen in FIG. 4 as the portion of data from zero (0) to approximately 50 microseconds on the time axis. In this region 28, the ultrasonic signals are influenced by the initial activation of the ultrasonic transducer and the recovery of the electronic circuits from the activation pulse.

Another region 30 that contains ultrasonic signals not related to the internal structure of the forging is the region near the backwall or through thickness of the forging. This region 30 of ultrasonic data is at 500 microseconds and beyond in FIG. 4. In region 30 there is a large signal that is the reflected echo from the back surface of the forging. This data region 30 is also removed, e.g., by partitioning or gating, from any measurement of the transition zone location, in step 52.

In the case of axisymmetric forgings, the ultrasonic waves travel from the periphery of a forging and through two transition zones (which are on opposites sides of the forging). The first transition zone is before the centerline of the forging and the second transition zone is after the centerline. To map the location of the transition zone in an axisymmetric forging, the signal region from the centerline 56 of the part and beyond may be removed (by partitioning or gating) from a measurement of the transition zone location. In the example shown in FIG. 4, the zone 58 corresponds to the internal region of the forging between the front surface and the centerline. This region 58 extends from approximately 50 microseconds to the centerline 56 of the forging at approximately 250 microseconds. Region 58 is suitable for analysis to locate the transition zone because the region has been gated or partitioned, and because the echo data has been corrected for the region.

A transition zone is detected by identifying the echo data in region 58 having an increased amount of ultrasonic scatter. Using the partitioned depth-corrected ultrasonic data in region 58 (see corrected trace 50), the location of the maximum echo signal(s) is identified, in step 62. The distance from this location to either the centerline of the forging for axisymmetric parts or to the opposite surface of the forging is calculated.

For the example shown in FIG. 4, the maximum amplitude 60 is located at 101 microseconds of signal time travel. This maximum echo signal for an internal region of the forging is taken to be indicative of a transition zone. The distance from the surface of the forging to the transition zone and back is calculated by, as shown in Equation A, multiplying the time value to the transition zone by the velocity of the material (for example, 0.23 inches/microsecond) and then dividing by two to correct for the round trip echo signal propagation zone. For the example shown in FIG. 4, the location of the transition zone from the front surface of the forging is 11.62 inches.

$$\text{Transition Zone Depth} = \frac{\text{Time to Peak Signal} * \text{Velocity}}{2} \quad (A)$$

Figure 6:
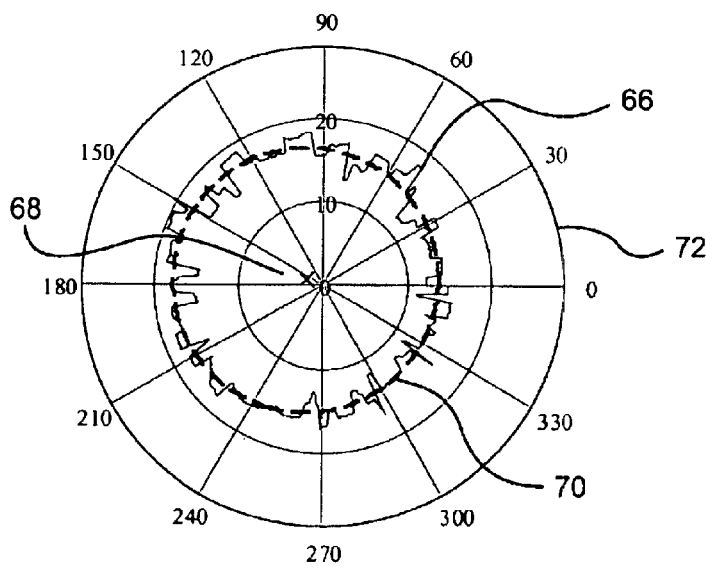
FIG. 6 is a polar chart mapping a transition zone in a cylindrical forging.

For axisymmetric forgings, the location of the transition zone can also be measured from the centerline of the forging. Using simple geometry, the location can be calculated as follows (Equation B):
(B) Transition Zone Radial Location=Forging Radius–Transition Zone Depth The position of the transition zone can be determined for each of the angular positions around the circumference of the forging in step 64. The transition zone 66 can be plotted in polar coordinates as is illustrated in FIG. 6.

The center of the transition zone is assumed to be the average of the transition zone locations around the circumference of the forging. Since the data is collected uniformly around the forging and not uniformly around the transition zone, the average location of the transition zone does not correspond to the center of the transition zone. The center of the transition zone is at twice the distance of the average of the zone locations from the center of the forging. The following equations (C and D) are used to determine and plot (step 69) the position of the center 68 of the transition zone:

$$X_{center} = 2 * \frac{\sum_{data} \text{Transition Zone Radial Location} * \cos(\text{circumferential angle})}{\text{number of data values}} \quad (C)$$

$$Y_{center} = 2 * \frac{\sum_{data} \text{Transition Zone Radial Location} * \sin(\text{circumferential angle})}{\text{number of data values}} \quad (D)$$

The transition zone shape at a defined axial location can be approximated as a circle 70 within the forging with a center located at the x and y coordinates calculated using Equations C and D.

Using the Pythagorean Theorem the average radius of the transition zone relative to the center of the zone can be calculated using the following Equation E:

$$\text{average radius} = \frac{\sum_{data} \sqrt{(TZ \text{ Location} * \cos(\text{angle}) - X_{center})^2 + (TZ \text{ Location} * \sin(\text{angle}) - Y_{center})^2}}{\text{number of data values}} \quad (E)$$

where the "TZ Location" is the transition zone radial location relative to the center of the forging; the "angle" is the circumferential angle around the forging at which the ultrasonic data was collected; the "data" is the set of ultrasonic data collected around the circumference of the forging, and the "number of data values" is the number of points along the circumference at which data was collected.

FIG. 6 shows an example of transition zone data 66 represented as a circle within the volume of a cylindrical forging 72. Maps of the transition zone can be printed by the computer 15 to plot the transition zone at each of the axial positions from which measurements were made. The computer may also combine the two-dimensional polar plots, such as shown in FIG. 6, from each of the axial positions to generate a three-dimensional map of the transition zone.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method to determine a depth of an internal feature in a forging using an ultrasonic transducer comprising:
    transmitting ultrasonic signals into the forging;
    collecting a first data set of echoes from internal areas of the forging having constant material properties;
    generating a correction factor from the first data set which compensates for attenuation of the echoes due to a depth in the forging at which the echoes are returned;
    collecting additional data on echoes reflected by the internal feature of ultrasonic signals transmitted into the forging;
    correcting the collected additional data to compensate for attenuation of the echoes and signals in the forging, wherein said correction includes applying the correction factor, and
    determining a depth of the internal feature in the forging.

2. A method as in claim 1 wherein the internal feature is a transition zone between a first metal alloy and a second metal alloy.

3. A method as in claim 1 wherein correcting the collected data further comprises compensating the data for attenuation of signal passing through the forging.

4. A method as in claim 1 wherein correcting the collected data further comprises applying a correction algorithm that is a function of signal transmission and echo reception.

5. A method as in claim 1 wherein correcting the collected data further comprises partitioning the data to eliminate echoes due to surfaces of the forging.

6. A method as in claim 1 wherein the data is collected at a plurality of angular positions around the periphery of the forging.

7. A method as in claim 1 wherein the data is collected at a plurality of angular positions around the periphery of the forging and at a plurality of axial positions along the forging.

8. A method to determine a depth of an internal feature in a forging having a generally circular cross section using an ultrasonic transducer comprising:
    transmitting ultrasonic signals into the forging;
    collecting data on echoes reflected by the internal feature of ultrasonic signals transmitted into the forging, wherein the data is collected at a plurality of angular positions around a perimeter of the forging;
    correcting the collected data to compensate for attenuation of the echoes and signals in the forging;
    partitioning the data to eliminate data corresponding to echoes from surfaces of the forging;
    identifying a maximum amplitude signal from the partitioned data for each of the angular positions;
    plotting the maximum amplitude signal data on polar chart and identifying a center of the maximum amplitude signal data, and
    plotting a circular cross-section of a transition zone coaxial with the center and a radius corresponding to an average value of the maximum amplitude signal data.

9. A method as in claim 8 further comprising repeating the steps for each of a plurality of axial positions on the forging.

10. A system to determine a depth of an internal feature in a forging comprising:
    an ultrasonic transducer positioned on a surface of the forging, wherein said transducer transmits ultrasound beams into the forging, receives echoes reflected from internal feature in the forging and generates data signals indicative of the echoes, and a computer receiving the data from the transducer, wherein said computer executes a program to process said data by applying a correction factor to the data to compensate for attenuation of the echoes and signals in the forging and to determine a depth of the internal feature in the forging, wherein said correction factor is determined from echo data collected from echoes returned from a portion of the for the forging having constant material properties.

11. A system as in claim 10 wherein said computer further comprises a printer for printing a plot of the depth of the internal feature.

* * * * *